United States Patent [19]

Singh et al.

[11] Patent Number: 5,458,879
[45] Date of Patent: Oct. 17, 1995

[54] ORAL VEHICLE COMPOSITIONS

[75] Inventors: Nikhilesh N. Singh, Mason; Anne M. Carella, Cincinnati; Ronald L. Smith, West Chester, all of Ohio

[73] Assignee: The Procter & Gamble Company, Cincinnati, Ohio

[21] Appl. No.: 316,172

[22] Filed: Sep. 30, 1994

Related U.S. Application Data

[63] Continuation-in-part of Ser. No. 205,665, Mar. 3, 1994, abandoned.

[51] Int. Cl.⁶ .................................................. A61K 9/08
[52] U.S. Cl. ..................... 424/400; 424/484; 424/486; 514/772; 514/772.2; 514/772.3; 514/772.5; 514/772.6; 514/781
[58] Field of Search ................................. 424/400, 486, 424/484; 514/772, 772.2, 772.3, 772.5, 772.6, 781

[56] References Cited

U.S. PATENT DOCUMENTS

| | | | |
|---|---|---|---|
| 4,226,848 | 10/1980 | Nagai et al. | 424/19 |
| 4,250,163 | 2/1981 | Nagai et al. | 424/14 |
| 4,427,681 | 1/1984 | Munshi | 424/260 |
| 4,576,645 | 3/1986 | Ravel et al. | 106/125 |
| 4,713,243 | 12/1987 | Schiraldi et al. | 424/151 |
| 4,894,238 | 1/1990 | Embry et al. | 424/486 |
| 4,988,679 | 1/1991 | Chavkin | 514/53 |
| 5,023,076 | 6/1991 | Ayer et al. | 424/78 |
| 5,079,009 | 1/1992 | Embrey et al. | 424/486 |
| 5,198,227 | 3/1993 | Batista et al. | 424/463 |
| 5,252,318 | 10/1993 | Joshi | 424/78.04 |

FOREIGN PATENT DOCUMENTS

0546810A1 6/1993 European Pat. Off. .

OTHER PUBLICATIONS

Nolan et al Agents & Actions 28, p. 53, 1989.

*Primary Examiner*—Gollamudi S. Kishore
*Attorney, Agent, or Firm*—David K. Dabbiere; Douglas C. Mohl; Jacobus C. Rasser

[57] ABSTRACT

Disclosed are oral pharmaceutical vehicle compositions comprising from about 0.05 to about 20% of a water-soluble mucoadhesive.

10 Claims, No Drawings

ORAL VEHICLE COMPOSITIONS

CROSS-REFERENCE TO RELATED APPLICATION

This is a continuation-in-part application of application Ser. No. 08/205,665, filed Mar. 3, 1994.

TECHNICAL FIELD

The present invention relates to oral pharmaceutical vehicle compositions.

BACKGROUND OF THE INVENTION

The cough reflex is an important mechanism whereby secretions from the lungs and airways are removed. Generally, such secretions are removed by the mucociliary escalator. However, when this mechanism is defective, or becomes overwhelmed by, for example, excessive secretions, cough then becomes a principal means of secretion removal.

The cough reflex is initiated by stimulation of mechanical receptors and is controlled by afferent pathways within the vagus (X), glossopharyngeal (IX), and superior laryngeal nerves to the cough center in the brainstem. Cough can be caused by, for example, foreign bodies, dust, mucus, debris, gases and smoke in the lower respiratory tract. Irritation of various sensory nerves in the nose, sinuses, pharynx, ears, stomach, pericardium or diaphragm can also produce coughing. In many of these conditions, chronic or paroxysmal cough, however, can be exhausting and debilitating, particularly when it interferes with sleep.

Oral cough preparations, such as tablets, lozenges, syrups, solutions, suspensions and the like, containing an effective antitussive agent have long been used for the symptomatic relief of coughs. The most popular of such preparations contain either dextromethorphan (or its hydrobromide salt) or codeine (or its sulfate salt) as the active antitussive agent. These treatments, among many others, are fully described in *Drug Evaluations*, 6th Ed., Chapter 21 (The American Medical Association, 1986).

Generally, cough syrups and sore throat medications have been available as pourable liquids or thixotropic gels. Exemplary prior art gel formulations for treatment of cough including those disclosed in U.S. Pat. nO. 4,427,681, incorporated herein by reference which use a suspending agent (Avicel/R R-591 from FMC Corporation) that give a thixotropic character to the formulation that is very viscous and needs a special device or an appropriate amount of shear forces through a dispensing nozzle to pour.

However, due to the nature of the action of the various active ingredients present in such syrups and medications, Applicants have found that it is highly desirable to have compositions which contain a mucoadhesive such as a poly(ethylene oxide) with specific physical characteristics which coat and adhere to the throat and mucous membrane and can thereby maintain an active ingredient in more intimate contact with the irritated area. Without being limited to theory, Applicants believe such compositions provide protection to the mucosal surfaces and thereby can treat or reduce the irritation, pain and discomfort associated with laryngopharyngitis ("sore throat") as well as mucosal irritation associated with esophagitis.

Prior art compositions containing these adhesive materials for pharmaceutical and medical applications include osmotic dosage forms as disclosed in U.S. Pat. Nos. 4,816,263, 4,837,111, WO 91-07173 and Brit. Pat. Appl. GB 2,189,995; buccal drug dosage forms, as disclosed in U.S. Pat. No. 4,764368; topical compositions for treating Acne Vulgaris, as disclosed in U.S. Pat. No. 4,335,028; a dosage form for administering nilvadipine for treating cardiovascular symptoms as disclosed in U.S. Pat. No. 4,902,514; pharmaceuticals for oral cavities, as disclosed in U.S. Pat. No. 4,649,043 and Japan, Kokei: 86-69338; chorhexidine gel for preventing infection in patients with radiation therapy; multi-unit delivery systems ad disclosed in U.S. Pat. No. 5,023, 088; sustained release tablets, as disclosed in U.S. Pat. No. 4,404, 183 and EP 277092; oral capsule containing aqueous and oil to control gastrointestinal transit time, as disclosed in U.S. Pat. No. 4,690,82; and low melting moldable pharmaceutical excipient, Canadian patent 2000697.

It is, therefore, an object of the present invention to provide such vehicle compositions which coat and adhere to mucous membranes such as the throat. It is still a further object of the present invention to provide such compositions which can treat the irritation, pain and discomfort associated with laryngopharyngitis and esophagitis. A further object of the present invention is to provide such vehicle compositions which, when used with a pharmaceutical active maintain the active ingredient in more intimate contact with the oral mucosa. These and other objects of this invention will become apparent in light of the following.

SUMMARY OF THE INVENTION

The present invention relates to oral pharmaceutical vehicle compositions. Specifically, the present invention relates to aqueous oral vehicle compositions comprising from about 0.05 to about 20% of a water-soluble mucoadhesive wherein said composition has an adhesive strength (measured as force of detachment) of from about 0.5 to about 10 Newton-sec, a tackiness of from about 1.0 to about 10 N, a co-efficient of viscoelasticity from about 0.20 to about 30 dynes/cm$^2$ and mechanical impedance of from about 0.15 to 0.6 measured between the frequency range of 1 to 10 Hz.

These compositions can have either a Newtonian or non-Newtonian flow. Newtonian compositions have a viscosity of from about 3 to about 100 cPs and non-Newtonian compositions have a viscosity of from about 100 to about 3000 cPs between the sheer rate between 1 to 200 per second.

The present invention also relates to solid dissolvable oral pharmaceutical mucoadhesive vehicle compositions which comprise from about 0.05 to about 20% of a water-soluble mucoadhesive polymer selected from the group consisting of poly(ethylene oxide), poly(ethylene glycol), poly(vinyl alcohol), poly(vinyl pyrrolidine), poly(acrylic acid), poly-(hydroxy ethyl methacrylate), hydroxyethyl ethyl cellulose, hydroxy ethyl cellulose and chitosan and mixtures thereof.

These compositions preferably comprise from about 0.02% w/v to about 5.00% w/v of a dispersant, preferably sodium carboxymethyl cellulose and also preferably further comprise one or more pharmaceutical actives, preferably a cough/cold active, at a level of from about .01% to about 50%.

All percentages and ratios used herein are by weight and all measurements are at 37° C., unless otherwise indicated.

DETAILED DESCRIPTION OF THE INVENTION

The term "mucoadhesive" as used herein refers to the phenomenon where a natural or synthetic bioadhesive applied to a mucosal epithelium adheres, usually creating a new interface, to the mucus layer. (*CRC Critical Reviews in Ther. Drug Carrier* Vol. 5 issue 1 (1988) pp. 21) Generally, mucoadhesion can be achieved via physical or chemical processes or both. This mechanism is described in J. Controlled Release Vol. 2 (1982) pp. 257 and in J. Controlled Release Vol. 18 (1992) pp. 249, both of which are incorporated by reference herein.

The term "viscoelasticity" as used herein is defined as the phenomenon whereby a material exhibits both a liquid-like and solid-like property under stress. Depending on the impact of shear-stress, a viscoelastic material can simultaneously behave both as a fluid and a solid. The fluid behavior is controlled by viscosity modulus, and the solid behavior is controlled by the elastic modulus. Once the shear-stress is removed, the viscoelastic materials tend to recover their original form. The extent to which it recovers its original form is dependent on the elastic component. The mechanical impedance is defined as a ratio of elastic modulus to complex modulus. The polymers described herein have a co-efficient of viscoelasticity from about 0.01 to 100 dynes/$cm^2$, more preferably from 0.1 to 50 dynes/$cm^2$ and most preferably from 0.20 to about 30 dynes/$cm^2$, co-efficient of elasticity from about 0.01 to 50 dynes/$cm^2$, more preferably from 0.03 to 30 dynes/$cm^2$ and most preferably from 0.07 to 18 dynes/$cm^2$ and mechanical impedance from about 0.15 to 0.6, more preferably from 0.3 to 0.6 and most preferably from 0.4 to 0.6 measured between the frequency range of 1 to 10 Hz.

The term "viscosity" as used herein is defined as the ratio of shear stress ($\tau$, dynes/$cm^2$) to shear rate ($\gamma$, $sec^1$). The compositions of the present invention can have either Newtonian or, preferably, a non-Newtonian flow. A material has a Newtonian flow if the shear stress increases linearly with the shear rate. The optimal viscosity range for the Newtonian compositions ranges from 3 to 200 cPs and most preferably from 50 to 100 cPs. The compositions have a non-Newtonian flow if the shear stress does not change linearly with shear rate. Therefore, a material with a non-Newtonian flow will have different viscosity values at different shear rates. Viscosity range for the non-Newtonian formulation ranges from 100 to 3000 $cPs^{n-1}$, most preferably from 400 to 1000$cPs^{n-1}$ between the sheer rates of 1 to 200 per second.

Flow and oscillatory tests for theological measurements described herein are based on a Carri-Med CSL 100 Controlled Stress Rheometer with a 4 cm, 2" cone/plate and double concentric measuring system. Detailed information and definitions on rheology can be found in "*Remingtons Pharmaceutical Sciences*" (Alfonso G. Gennaro editor) pp. 331; *Physical Pharmacy* (Alfred Martin, editor) pp. 453 and *The Theory and Practice of Industrial Pharmacy* (Leon Lachmann et al, editor) pp. 123; all of which are incorporated herein by reference.

The adhesive strength (measured as work of adhesion) of the mucoadhesives used herein generally ranges from 0.5 to 10 Newton-sec, more preferable from 1 to 8 Newton-sec, and most preferable from 3 to 7N s and tackiness of from about 1 to about 10 Newton as measured using the TA.XT2 Texture Analyzer (Scarsdale N.Y.) instrument using a TA-25 2" diameter probe at 25° C. The instrument probe is set to operate at a withdrawal and penetration rates of 0.1 mm/sec., and a withdrawal point of 5 mm. The test material (0.1) is placed on an aluminum block and compressed by the probe at an applied force of 0.5 Newton for 5 sec and data is collected on an IBM compatible computer equipped with an analog to digital serial card and running the XTRA Dimenion software package (Stable Micro Systems). The work of adhesion is calculated using the force/time curve. Also recorded is the peak resistance curve.

Preferred polymers for use in both the aqueous and solid dissolvable mucoadhesive compositions of the present invention include the following hydrogels: poly(ethylene oxide), poly(ethylene glycol), poly(vinyl alcohol), poly(vinyl pyrrolidine), poly(acrylic acid), poly(hydroxy ethyl methacrylate), hydroxypropyl cellulose, hydroxypropyl methyl cellulose, hydroxyethyl methyl cellulose, hydroxyethyl cellulose, and chitosan and mixtures thereof. The techniques, compositions for making hydrogels, and other fundamentals are discussed in "Hydrogels in Modern Medicine & Pharmacy Volume 1 (N. A. Peppas ed.) PP 1 to 171 (CRC Press, 1988) incorporated herein by reference.

These polymers are generally commercially available as follows: the polymers of poly(ethylene oxide) are available as Polyox® from Union Carbide Corporation; poly(ethylene glycol), also known as PEG is available as Macrogol® from Ashland Corp.; poly (vinyl alcohol) is available from E. I. du Pont de Nemours & Co.; poly(vinyl pyrrolidine) is available from BASF Wyandotte Corp., and GAF Corp.; hydroxypropyl cellulose is available as Klucel from Shin-Etsu Chem. Co.; hydroxypropyl methyl cellulose or methyl hydroxypropylcellulose, and hydroxyethyl methyl cellulose are all available from Dow Chemicals. Sodium carboxy methyl cellulose is available from FMC Corp. The polymers are described in "*Handbook of Pharmaceutical Excipients*" jointly published by American Pharmaceutical Association (Washington D.C. 20037, U.S.A.) and The Pharmaceutical Society of Greater Britain (London SE 17JN, England), and is incorporated by reference herein.

The most preferred for use herein is poly(ethylene oxide) and has the following chemical structure:

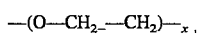

$$-(O-CH_2-CH_2)-_x.$$

These polymers are commercially available under the trade name "Polyox Water Soluble Resins" from Union Carbide Corporation. Generally they are available with average molecular weights from as low as 200 up to 10,000,000. However, most of the products below 25,000 are viscous liquids or waxy solids commonly referred to as poly(ethylene glycols). Most preferred poly(ethylene oxide) polymers used herein have an average molecular weight from about 300,000 to 10,000,000. They are dry free-flowing white powders, completely soluble in water at temperatures up to 98° C.

The compositions of the present invention comprise from about 0.05% to 20% w/v and most preferable from 0.2% to 0.5% w/v of the mucoadhesive.

Optional Components

The vehicle compositions of the present invention preferably employ a dispersing agent. The most preferred dispersing agent for use herein is sodium carboxymethyl cellulose.

The amount of dispersing agent employed in the compositions of this invention is from about 0.5% to about 5%, more preferably from 1% to 5%, based on the total composition.

The compositions of the present invention also preferably include at least one oral pharmacological active preferably selected from the following classes: (a) analgesic agents, (b) decongestants, (c) expectorants, (d) antitussives, (e) antihistamines and (f) gastrointestinal agents. The analgesics useful for this invention include acetaminophen, acetyl salicylic acid, indomethacin and optically active isomers or racemates of ibuprofen, naproxen, flurbiprofen, carprofen, tiaprofenic acid, cicloprofen, ketoprofen, ketorolac, etodolac, indomethacin, sulindac, fenoprofen, diclofenac, piroxicam, benzydomine, nabumetone, their pharmaceutically acceptable salts and mixtures thereof. The decongestants prepared for use in the compositions of the present invention include pseudoephedrine, phenylpropanolamine, phenylephrine and ephedrine, their pharmaceutically acceptable salts, and mixtures thereof. The antitussives preferred for use in the present invention include those such as dextromethorphan, chlophedianol, carbetapentane, caramiphen, noscapine, diphenhydramine, codeine, hydrocodone, hydromorphone, fominoben, benzonatate, their pharmaceutically-acceptable salts, and mixtures thereof. The expectorants (also known as mucolytic agents) preferred for use in the present invention include glyceryl guaiacolate, terpin hydrate, ammonium chloride, N acetylcysteine and bromhexine, ambroxol, their pharmaceutically acceptable salts, and mixtures thereof. All of these components, as well as their acceptable dosage ranges are described in the following: U.S. Pat. No. 4,783,465 to Sunshine et al., issued Nov. 8, 1988, U.S. Pat. No. 4,619,934 to Sunshine et al., issued Oct. 28, 1986, which are incorporated by reference herein. Also useful herein are topical anesthetics such as phenol, lidocaine, dyclonine, benzocaine, menthol, benzyl alcohol, salicyl alcohol, and hexylresorcinol, their pharmaceutically-acceptable salts, and mixtures thereof.

Examples of gastrointestinal agents preferred for use in the present invention include anticholinergics, including: atropine, clidinium and dicyclomine; antacids, including aluminum hydroxide, bismuth subsalicylate, bismuth subcitrate, simethicone, calcium carbonate and magaldrate; $H_2$-receptor antagonists, including: cimetidine, famotidine, nizatidine and ranitidine; laxatives, including: phenolphthalein and casanthrol; gastroprotectants including sucralfate and sucralfate humid gel; gastrokinetic agents including metoclopramide and eisaprode; proton pump inhibitors including omeprazole and antidiarrheals including: diphenoxylate and loperamide.

Also useful are bronchodilators such as terbutaline, aminophylline, epinephrine, isoprenaline, metaproterenol, bitoterol, theophylline and albuterol. A highly preferred optional component is caffeine.

The term "pharmaceutically acceptable salts" refers to salts prepared from pharmaceutically acceptable non-toxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

The mucoadhesive polymers can be incorporated into various solid or chewable oral compositions such as tablets, lozenges, troches and granules. These solid forms dissolve in the mouth and thereby coat and adhere to the mucous membranes. Tablets can be compressed, tablet triturates, enteric-coated, sugarcoated, film-coated or multiple compressed, containing suitable binders, lubricants, diluents, disintegrating agents, coloring agents, flavoring agents, preservatives and flow-inducing agents. Suitable solid dosage forms can incorporate effervescent or other water-dispersible substances and dried into dosage forms that rapidly disintegrate upon coming into contact with an aqueous liquid. Suitable effervescent technology is described in Chapter 6 of *Pharmaceutical Dosage Forms: Tablets*, Vol. I, $2^{nd}$ ed., A Lieberman ed., 1989, Marcel Dekker, Inc. herein incorporated by reference. Methods of solid dosage formulation are well known in the art and any appropriate method may be utilized. Further information regarding solid dosage formulation can be found in *Remington's Pharmaceutical Sciences*, pp. 1633–1664, (Alfonso R. Gennaro, editor) (18th ed. 1990).

Also useful are freeze dried dosage forms. A preferable method of freezing and drying is to fast freeze the composition and then dry the composition to a final moisture content of about 2% to about 5%. Suitable methods of freeze-drying and production are taught by U.S. Pat. No. 4,642,903, Feb. 17, 1987, to Davies, U.S. Pat. No. 4,946,684, Aug. 7, 1990, to Blank et al., U.S. Pat. Nos. 4,305,502 and 4,371,516, issued Dec. 15, 1981 and Feb. 1, 1983 respectively, to Gregory et al., and U.S. Pat. No. 5,188,825, Feb. 23, 1993, to Iles et al.; which are all incorporated herein by reference.

Similarly, the compositions of the present invention may be vacuum dried. Vacuum drying involves at least the partial drying of compositions at temperatures above compositions' collapse temperature. Freeze drying, on the other hand, involves the drying of compositions at temperatures below the compositions collapse temperature. Any suitable method of vacuum drying may be used. Suitable vacuum drying processes are described in U.S. Pat. No. 5,298,261, to Pebley et al., issued Mar. 29, 1994, herein incorporated by reference.

One other form of fast dissolving technology that may be applicable to the present invention is a liquid/liquid extract developed by Janssen Pharmaceutica Inc. and is identified by the trade name Quicksolv™. This technology is fully described in U.S. Pat. No. 5,215,756 herein incorporated by reference.

The mucoadhesive polymers can be incorporated into various liquid oral compositions such as syrups, gels, emulsions, pseudo-emulsions, micro-emulsions and suspensions. These compositions comprise effective amounts of the mucoadhesive, usually at least about 0.1% to about 0.5% and therapeutically active components from about 0.01% to 50% and more preferably from 0.5% to 25% of the formulation. The mucoadhesive hydrogel vehicle or the compositions also include solutions or suspensions reconstituted from powders or granules. The aqueous vehicles and compositions also contain suitable amounts of preservatives, emulsifying agents, suspending agents, diluents, sweeteners, taste-masking agents, coloring agents, and flavoring agents.

Specific examples of pharmaceutically acceptable carriers and excipients that may be used to formulate oral dosage forms, are described in U.S. Pat. No. 3,903,297, Robert, issued Sep. 2, 1975, incorporated by reference herein.

In preparing the liquid oral dosage forms, the active component is incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. The most preferred carrier is a suspension of the pharmaceutical composition in an aqueous vehicle. Such suspending agents are well known to those skilled in the art. While the amount of water in the compositions of this invention can vary over quite a wide range depending upon the total weight and volume of the active component and other optional non-active ingredients, the total water content, based on the weight of the final composition, will generally range from about 10 to about 75%, and, preferably, from about 20 to about 40%, by weight/volume. Methods for preparations and manufacture of solutions, suspensions, and emulsions are discussed in *Remington's Pharmaceutical Sciences* (Alfonso R. Gennaro, editor), pp. 1519, incorporated herein by reference.

Although water itself may make up the entire carrier, typical liquid formulations preferably contain a co-solvent, for example, propylene glycol, corn syrup, glycerin, sorbitol solution and the like, to assist solubilization and incorporation of water-insoluble ingredients, such as flavoring oils and the like into the composition. In general, therefore, the compositions of this invention preferably contain from about 1 to about 70% v/v and, most preferably, from about 5 to about 50% v/v, of the co-solvent.

In addition, the present invention may optionally incorporate a cooling agent or a combination of cooling agents. Suitable cooling agents include, for example, menthol as well as those described in U.S. Pat. No. 4,136,163, Jan. 23, 1979, to Watson et al., U.S. Pat. No. 4,230,668, Oct. 28, 1980, to Rowsell et al. and U.S. Pat. No. 4,032,661, to Rowsell et al., all of which are herein incorporated by reference. A particularly preferred cooling agent is N-ethyl-p-menthane-3-carboxamide (WS-3 supplied by Sterling Organics), taught by the above incorporated U.S. Pat. No. 4,136,163. Another particularly preferred cooling agent is 3-1-menthoxypropane 1,2-diol (TK-10 supplied by Takasago Perfumery Co., Ltd., Tokyo, Japan). This material is described in detail in U.S. Pat. No. 4,459,425, Jul. 10, 1984 to Amano et al. and incorporated herein by reference.

Other optional ingredients well known to the pharmacist's art may also be included in amounts generally known for these ingredients, for example, natural or artificial sweeteners, flavoring agents, colorants and the like to provide a palatable and pleasant looking final product, antioxidants, for example, butylated hydroxy anisole or butylated hydroxy toluene, and preservatives, for example, methyl or propyl paraben or sodium benzoate, to prolong and enhance shelf life.

Methods

The amount of the pharmaceutical composition administered depends upon the percent of active ingredients within its formula, such as an analgesic, decongestant, cough suppressant, expectorant, antihistamine and/or gastrointestinal active required per dose, stability, release characteristics and other pharmaceutical parameters.

Usually from about 1 mg/kg to about 500 mg/kg per day, preferably from about 5 mg/kg to about 300 mg/kg per day and most preferably from about 5 mg/kg per day to about 200 mg/kg per day of the pharmaceutical composition is administered as described herein. This amount can be given in a single dose, or, preferably, in multiple (two to six) doses repeatedly or sustained release dosages over the course of treatment. Generally, each individual dosage of the pharmaceutical compositions of the present invention range from about 1 mg/kg to about 25 mg/kg, preferably from about 2 mg/kg to about 15 mg/kg and most preferably from about 3 mg/kg to about 10 mg/kg. While dosages higher than the foregoing may be effective, care must be taken, as with any drug, in some individuals to prevent adverse side effects.

The following examples illustrate embodiments of the subject invention wherein both essential and optional ingredients are combined.

EXAMPLE I

A liquid composition for oral administration is prepared by combining the following ingredients:

| Ingredient | % W/V |
|---|---|
| Poly (ethylene oxide)(molecular wt = 5,000,000)[1] | 0.450 |
| Sodium carboxymethyl cellulose | 0.450 |
| Sodium citrate | 0.522 |
| Citric Acid | 0.338 |
| Corn Syrup | 40.000 |
| Colorants | 0.008 |
| Flavor | 0.500 |
| Alcohol 95% | 5.000 |
| Water, Purified QS | 100.000 |

[1]Polyox WSR Coag from Union Carbide

The purified water (approximately 10% of the final batch volume) is poured into a batch container equipped with a disperser. The sodium citrate, and citric acid is added sequentially and dissolved with agitation. In a separate container the flavors are dissolved in alcohol and added to the first mixture while stirring. In a separate container the colorants are added to purified water (approximately 0.5% of the final batch volume). This colorant solution is then added to the first batch container. In a separate container, sodium carboxymethyl cellulose, and polyox WSR Coag is sequentially dispersed in propylene glycol using medium shear. The propylene glycol mixtures, and corn syrup are added to the first container and stirred until homogeneous. The remaining QS purified water is added to the resulting mixture and stirred.

The composition will have a non-Newtonian viscosity of 700 $cPs^{n-1}$ measured between the shear-rates of 0.5 to 40 per sec., an adhesive strength of 1.30 Newton-sec, and tackiness of 4.5 Newton. The mechanical impedance of the product is 0.4, coefficient viscosity 1.10, and the coefficient of viscoelasticity is 20.0.

Administration of 10 ml to 20 ml (2 to 4 teaspoonsful) to a person in need of treatment provides improved relief from the irritation, pain and discomfort associated with laryngopharyngitis ("sore throat") as well as mucosal irritation associated with esophagitis.

EXAMPLE II

A liquid composition for oral administration for relief from symptoms, aches and pain associated with cough, cold, and flu is prepared by combining the following ingredients:

| Ingredient | % W/V |
|---|---|
| Acetaminophen | 5.000 |
| Alcohol (95%) | 5.000 |
| Poly (ethylene oxide)(molecular wt = 5,000,000) | 0.450 |
| Sodium carboxymethyl cellulose | 0.450 |
| Pseudoephedrine HC | 10.300 |
| Propylene Glycol | 15.000 |

-continued

| Ingredient | % W/V |
|---|---|
| Sodium Citrate | 0.522 |
| Citric Acid | 0.338 |
| Liquid Sugar (Simple Syrup) | 40.000 |
| Colorants | 0.008 |
| Flavor | 0.500 |
| Water, Purified QS | 100.000 |

[1]Polyox WSR Coag from Union Carbide

The purified water (approximately 10% of the final batch volume) is poured into a batch container equipped with a disperser. The sodium citrate, citric acid, and actives other than acetaminophen are added sequentially and dissolved with agitation. In a separate mixture the flavors are dissolved in alcohol and added to the first mixture while stirring. In a separate container the colorants are added to purified water (approximately 0.5% of the final batch volume). This colorant solution is then added to the first batch container. In a separate container, sodium carboxymethyl cellulose, acetaminophen and polyox WSR COAG is sequentially added to propylene glycol while stirring. The propylene glycol mixtures, liquid sugar (simple syrup) are added to the first container and stirred until homogeneous. The remaining purified QS water is added to the resulting mixture and stirred.

The composition will have a non-Newtonian viscosity of 770 $cPs^{n-1}$ measured between the shear-rates of 0.5 to 40 per sec., an adhesive strength of 1.68 Newton-sec, and tackiness of 5.0 Newton. The mechanical impedance of the product is 0.4, coefficient of elasticity 1.05, and the coefficient of viscoelasticity is 27.7.

Administration of 10 ml to 20 ml (2 to 4 teaspoonsful) to a person in need of treatment provides improved relief from cough, cold-like, flu and flu-like symptoms.

EXAMPLE III

A liquid composition for oral administration for treatment of cough is prepared by combining the following ingredients:

| Ingredients | Amount (W/V) |
|---|---|
| Dextromethorphan HBr | 0.133 |
| High fructose corn syrup | 45.000 |
| Tween 60 | 0.500 |
| Tween 80 | 0.500 |
| Propylene glycol | 9.000 |
| Sodium carboxymethyl cellulose | 0.0450 |
| Poly (ethylene oxide) (molecular wt = 5,000,000) | 0.300 |
| Potassium sorbate | 0.100 |
| Alcohol 95% v/v | 5.000 |
| Natural menthol | 0.050 |
| Sodium citrate | 0.522 |
| Citric acid, anhydrous | 0.338 |
| Saccharin, sodium | 0.025 |
| Aspartame | 0.200 |
| Flavor | 0.844 |
| TK-10 | 0.010 |
| WS-3 | 0.012 |
| FD&C Red #40 | 0.030 |
| Water, purified | qs 100 |

[1]Polyox WSR Coag from Union Carbide

The corn syrup is poured into a batch container equipped with a Lightning' mixer. The tween 60, tween 80, sodium citrate, citric acid, are added sequentially and dissolved with agitation. In a separate container the colorants are added to purified water (approximately 0.5% of the final batch volume). This colorant solution is then added to the first batch container. In a separate container, the flavors including natural menthol are added to alcohol. The resulting mixture is stirred until homogeneous and then added to the first container. In a separate container the dextromethorphan HBr, sodium carboxymethyl cellulose and polyox WSR COAG are added to the propylene glycol while stirring. The propylene glycol mixture is then added to the first batch and stirred until homogeneous. The remaining purified QS water is added to the resulting mixture and stirred.

The composition will have a non-Newtonian viscosity of 650 $cPs^{n-1}$ measured between the shear-rates of 0.5 to 40 per sec., an adhesive strength of 1.07 Newton-sec, and tackiness of 4.8 Newton. The mechanical impedance of the product is 0.4, coefficient of elasticity is 1.20, and the coefficient of viscoelasticity is 23.

Administration of 10 ml to 20 ml (2 to 4 Teaspoonsful) to a person in need of treatment from cough.

EXAMPLE IV

A liquid composition for oral administration for relief from symptoms and pain, associated with cough, cold, and flu is prepared by combining the following ingredients:

| Ingredients | % W/V |
|---|---|
| Dextromethorphan HBr | 0.133 |
| Guafenesin | 1.333 |
| Pseudoephedrine HCl | 0.300 |
| (R,S) Ibuprofen | 1.000 |
| High fructose corn syrup | 45.000 |
| Tween 60 | 0.500 |
| Tween 80 | 0.500 |
| Propylene glycol | 9.000 |
| Sodium Carboxymethyl cellulose | 0.450 |
| Poly (ethylene oxide)(molecular wt = 5,000,000) | 0.300 |
| Potassium sorbate | 0.100 |
| Alcohol 95% v/v | 5.000 |
| Natural menthol | 0.050 |
| Sodium citrate | 0.522 |
| Citric acid, anhydrous | 0.338 |
| Saccharin, sodium | 0.025 |
| Aspartame | 0.200 |
| Flavor | 0.844 |
| TK-10 | 0.010 |
| WS-3 | 0.012 |
| FD&C Red #40 | 0.030 |
| Water, purified | qs 100 |

[1]Polyox WSR Coag from Union Carbide

The corn syrup is poured into a batch container equipped with a Lightnin' mixer. The tween 60, tween 80, sodium citrate, and citric acid are added sequentially and dissolved with agitation. In a separate container the colorants are added to purified water (approximately 0.5% of the final batch volume). This colorant solution is then added to the first batch container. In a separate container, the flavors including natural menthol are added to alcohol. The resulting mixture is stirred until homogeneous and then added to the first container. In a separate container the dextromethorphan HBr, guaifenesin, (S,R) ibuprofen and polyox WSR 301 are added to the propylene glycol while stirring. The propylene glycol mixture is then added to the first batch and stirred until homogeneous. The remaining purified QS water is added to the resulting mixture and stirred.

The composition will have a non-Newtonian viscosity of 360 cPs$^{n-1}$ measured between the shear-rates of 0.5 to 40 per sec., an adhesive strength of 1.80 Newton-sec, and tackiness of 5.3 Newton. The mechanical impedance of the product is 0.4, coefficient of elasticity is 1.45, and the coefficient of viscoelasticity is 14.

Administration of 10 ml to 20 ml (2 to 4 Teaspoonsful) to a person in need of relief from symptoms of cough, cold and flu.

EXAMPLE V

A liquid composition for oral administration for relief from symptoms and pain, associated with cough, cold, and flu is prepared by combining the following ingredients:

| Ingredients | % W/V |
| --- | --- |
| Dextromethorphan HBr | 0.133 |
| Guafenesin | 1.333 |
| S(+)- Ibuprofen | 1.000 |
| High fructose corn syrup | 45.000 |
| Tween 60 | 0.500 |
| Tween 80 | 0.500 |
| Propylene glycol | 9.000 |
| Sodium Carboxymethyl cellulose | 0.450 |
| Poly (acrylic acid) polymer[1] | 0.300 |
| Potassium sorbate | 0.100 |
| Alcohol 95% v/v | 5.000 |
| Natural menthol | 0.050 |
| Sodium citrate | 0.522 |
| Citric acid, anhydrous | 0.338 |
| Saccharin, sodium | 0.025 |
| Aspartame | 0.200 |
| Prosweet Liquid | 0.200 |
| Flavor, Watermelon | 0.020 |
| Flavor, Cherry | 0.520 |
| Flavor Cherry | 0.104 |
| TK-10 | 0.010 |
| WS-3 | 0.012 |
| FD&C Red #40 | 0.030 |
| Water, purified | qs 100 |

[1]Available as Carbopol 934P from B. F. Goodrich Corp.

The corn syrup is poured into a batch container equipped with a Lightnin' mixer. The tween 60, tween 80, sodium citrate, and citric acid are added sequentially and dissolved with agitation. In a separate container the colorants are added to purified water (approximately 0.5% of the final batch volume). This colorant solution is then added to the first batch container. In a separate container, the flavors including natural menthol are added to alcohol. The resulting mixture is stirred until homogeneous and then added to the first container. In a separate container the dextromethorphan HBr, guaifenesin, (S)-ibuprofen, sodium carboxymethyl cellulose and carbopol 934P are added to the propylene glycol while stirring. The propylene glycol mixture is then added to the first batch and stirred until homogeneous. The pH of the mixture is adjusted to 6.0 and then the remaining purified QS water is added to the resulting mixture and stirred.

The composition will have a non-Newtonian viscosity of 250 cPs$^{n-1}$ measured between the shear-rates of 0.5 to 150 per sec., an adhesive strength of 1.15 Newton-sec, and tackiness of 5.0 Newton. The mechanical impedance of the product is 0.4, coefficient of elasticity is 1.25, and the coefficient of viscoelasticity is 6.50.

Administration of 10 ml to 20 ml (2 to 4 Teaspoonsful) to a person in need of relief from symptoms of cough, cold and flu.

EXAMPLE VI

A liquid composition for oral administration for relief from symptoms and distress of heartburn, diarrhea, indigestion, upset stomach, and nausea.

| Ingredients | % w/v |
| --- | --- |
| Bismuth subsalicylate slurry | 18.140 |
| Methyl cellulose | 1.090 |
| Magnesium aluminum silicate | 0.990 |
| Poly (ethylene oxide)(mol. wt = 4,000,000) | 0.300 |
| Sodium carboxymethyl cellulose | 0.450 |
| Methyl salicylate | 0.080 |
| Salicylic acid | 0.070 |
| Sodium saccharin | 0.060 |
| Benzoic acid | 0.020 |
| Sorbic acid | 0.012 |
| D&C red no. 22 | 0.007 |
| D&C red no. 28 | 0.005 |
| Purified water | qs 100 |

[1]Available as Polyox WSR 301 from Union Carbide

The bismuth subsalicyalte slurry, methyl cellulose and magnesium subsalicylate are suspended in purified water in a batch container equipped with a Lightnin' mixer. In a separate batch container, Polyox 301, sodium carboxymethyl cellulose, methyl salicylate, sodium saccharin, salicylic acid, benzoic acid, and sorbic acid is dissolved in propylene glycol along with the dye solutions. The mixture from the second container is then added to the slurry in the first batch container. The mixture is made to volume and stirred.

The composition has apparent viscosity of 500 cPs$^{n-1}$, between the shear rate of 0.5 to 150 per sec. The adhesive strength of the composition is 1.30 Newton-sec, and tackiness of 5.00 Newtons. The mechanical impedance of the composition is 0.40, coefficient of elasticity is 1.09 and coefficient of viscoelasticity is 10.

Administration of 10 ml to 20 ml (2 to 4 Teaspoonsful) to a person in need of relief from distress due to gastrointestinal symptoms.

EXAMPLE VII

A chewable tablet for oral administration for treating cough is produced by combining the following ingredients:

| Ingredient | % w/w |
| --- | --- |
| Dextromethorphan HBr adsorbate (10%) | 200 mg |
| Polyox WSR 1105 | 20 mg |
| Maltodextrin | 50 mg |
| Crystalline sorbitol | 1000 mg |
| Magnesium stearate | 1 mg |
| Color & Flavor | qs |

The dextromethorphan HBr adsorbate and Polyox WSR 1105 are granulated with a 10% w/w solution of maltodextrin. The resulting granule is dried at a temperature of about 45° C. overnight. The dry granule is milled and blended with the remaining components. The resulting powder blend is compressed into a 1.20 g tablet as is conventional in the art. One tablet is administered to a human in need of treatment, thereby reducing cough.

Upon dissolution in the mouth, the composition has apparent viscosity of 500 cPs$^{n-1}$, between the shear rate of 0.5 to 150 per sec. The adhesive strength of the composition is 1.30 Newton-see, and tackiness of 5.00 Newtons. The mechanical impedance of the composition is 0.40, coefficient of elasticity is 1.09 and coefficient of viscoelasticity is 10.

Substantially similar results are obtained when the dextromethorphan is replaced with therapeutically equivalent level of chlophedianol, carbetapentane, caramipen, noscapine, diphenhydramine, codeine, hydrocodone, hydromorphone, fominoben, their pharmaceutically acceptable salts, and their mixtures thereof.

EXAMPLE VIII

An effervescent tablet for treating cough and soothing sore throat is produced by combining the following ingredients:

| Ingredients | % w/v |
| --- | --- |
| Dextromethorphan HBr adsorbate | 200 mg |
| Polyox WSR 301 | 20 mg |
| Citric Acid, anhydrous (granular) | 1180 mg |
| Sodium bicarbonate (granular) | 1700 mg |
| Sodium bicarbonate (powder) | 175 mg |
| Flavor qs | |
| Water | 30 mg |

Thoroughly blend dextromethorphan adsorbate, polyox WSR 301, citric acid and sodium bicarbonate (powder) in a planetary mixture. Quickly add all of the water and mix until a workable mass is formed. Granulate through a 10 mesh screen using an oscillating granulator. Spread evenly on a paper-lined drying tray and dry in a forced-draft oven at 70° C. for 2 hr. Remove from oven, cool, and regranulate through a 16 mesh screen. Place granulation in a tumble blender and add sodium bicarbonate (granular). Mix well. Compress in a 1-in., flat-faced beveled-edge tablets (about 3.00 g each). Administer 1 tablet to human for treating cough.

Upon dissolution in the mouth, the composition has apparent viscosity of 500 $cPs^{n-1}$, between the shear rate of 0.5 to 150 per sec. The adhesive strength of the composition is 1.30 Newton-sec, and tackiness of 5.00 Newtons. The mechanical impedance of the composition is 0.40, coefficient of elasticity is 1.09 and coefficient of viscoelasticity is 10.

Substantially similar results are obtained when the dextromethorphan is replaced with therapeutically equivalent level of chlophedianol, carbetapentane, caramipen, noscapine, diphenhydramine, codeine, hydrocodone, hydromorphone, fominoben, their pharmaceutically acceptable salts, and their mixtures thereof.

What is claimed is:

1. An aqueous oral liquid pharmaceutical mucoadhesive composition consisting essentially of:
    (a) from about 0.05 to about 20% of a water-soluble mucoadhesive polymer selected from the group consisting of poly(ethylene oxide), poly(ethylene glycol), poly(vinyl alcohol), poly(vinyl pyrrolidine), poly(acrylic acid), poly(hydroxy ethyl methacrylate), hydroxyrpropyl cellulose, hydroxyethyl ethyl cellulose, hydroxyethyl ethyl cellulose and chitosan and mixtures thereof,
    (b) from about 0.02% w/v to about 5% w/v of sodium carboxymethyl cellulose; and
    (c) one or more pharmaceutically active agents wherein said composition has an adhesive strength (measured as force of detachment) of from about 0.5 to about 10 Newtons-sec, a tackiness of from about 1.0 to about 10N, a coefficient of viscoelasticity from about 0.20 to about 30 dynes/$cm^2$ and mechanical impedance of from about 0.15 to 0.6 measured between the frequency range of 1 to 10 Hz.

2. A pharmaceutical composition according to claim 1 wherein said mucoadhesive is poly(oxyethylene oxide) having a molecular weight of from about 2000 to about 10,000,000.

3. A pharmaceutical vehicle composition according to claim 1 which has a Newtonian viscosity of from about 3 to about 100 cPs.

4. A pharmaceutical vehicle composition according to claim 2 wherein said composition has a non-Newtonian viscosity of from about 100 to 300 $cPs^{n-1}$ at the shear rate between 1 to 200 per sec.

5. A pharmaceutical composition according to claim 4 wherein said pharmaceutically active agent is selected from the group consisting of analgesics, decongestants, expectorants, antitussives, antihistamines, anticholinergics, antacids, gastroprotectants, $H_2$-receptor antagonists, laxative, gastrokinetics, proton pump inhibitors, antidiarrheals and mixtures thereof.

6. A pharmaceutical composition according to claim 5 wherein said analgesic is selected from the group consisting of aspirin, acetaminophen, acetylsalicylic acid, ibuprofen, naproxen, flurbiprofen, carprofen, tiaprofenic acid, ciclopro-fen, ketoprofen, ketorolac, etodolac, indomethacin, sulindac, fenoprofen, diclofenac, piroxicam, nabumetone, pharmaceutically acceptable salts thereof, optically active isomers thereof and mixtures thereof; decongestants selected from the group consisting of pseudoephedrine, phenylpropanolamine, phenylephrine and ephedrine, pharmaceutically acceptable salts thereof and mixtures thereof; expectorants selected from the group consisting of glyceryl guaicolate, terpin hydrate, ammonium chloride, N-acetylcysteine, bromhexine, vasicine, ambroxol, carbocistein, sobrerol, pharmaceutically acceptable salts thereof and mixtures thereof; antitussives selected from the group consisting of dextromethorphan, chlophedianol, carbetapentane, caramiphen, noscapine, diphenhydramine, codeine, hydrocodone, hydromorphone, fominoben, and phenol, pharmaceutically acceptable salts thereof and mixtures thereof; antihistamines selected from the group consisting of chlorpheniramine, brompheniramine, dexchlorpheniramine, dexbrompheniramine, triprolidine, doxylamine, tripelennamine, cuproheptadine, carbinoaxime, doxylamine, bromdiphenhydramine, pyrilamine, acrivastine, rocastine, phenindamine, astemizole, azatadine, azelastine, cetirizine, ebastine, ketotifen, lodoxine, loratidine, levocabastine, mequitazine, oxatomide, setastine, tazifyline, temelastine terfenadine, and terfenadine carboxylate, pharmaceutically acceptable salts thereof and mixtures thereof; anticholinergics selected from the group consisting of atropine, clidinium and dicyclomine; antacids selected from the group consisting of aluminum hydroxide, bismuth subsalicylate, bismuth subcitrate, simethicone, calcium carbonate, magaldrate, $H_2$-receptor antagonists selected from the group consisting of cimetidine, famotidine, nizatidine and ranitidine; laxatives selected from the group consisting of phenolphthalein and casanthrol; and antidiarrheals selected from the group consisting of diphenoxylate and loperamide and mixtures thereof.

7. A pharmaceutical composition according to claim 6 which further comprises an aromatic agent selected from the group consisting of menthol, eucalyptus oil, camphor, L-menthyl acetate, N-ethyl-p-menthane-3-carboxamide, N, 2,3-trimethyl-2-isopropylbutanamide, 3- and L-menthoxypropane 1,2 diol and mixtures thereof.

8. A method for the treatment of cough in humans or animals in need of such relief comprising the administration of a safe and effective amount of the composition of claim 7.

9. A method for the treatment of or reducing the irritation, pain and discomfort associated with laryngopharyngitis in humans or animals in need of such relief comprising the administration of a safe and effective amount of the composition of claim 7.

10. A method for the treatment of upper gastrointestinal disorders in humans or animals in need of such relief comprising the administration of a safe and effective amount of the composition of claim 7.

* * * * *

UNITED STATES PATENT AND TRADEMARK OFFICE
CERTIFICATE OF CORRECTION

PATENT NO. : 5,458,879
DATED : October 17, 1995
INVENTOR(S) : Nikhilesh N. Singh, et al.

It is certified that error appears in the above-identified patent and that said Letters Patent is hereby corrected as shown below:

<u>Column 2,</u>
Line 49, "3000 cPs" should be -- 3000 $cPs^{n-1}$ --.

<u>Column 12,</u>
Line 32, (Example VI), after "apparent", insert -- non-Newtonian --.
Line 66, (Example VII), after "apparent", insert -- non-Newtonian --.

<u>Column 13,</u>
Line 41, (Example VIII), after "apparent", insert -- non-Newtonian --.

<u>Column 14,</u>
Line 17 (Claim 4), "100 to 300 $cPs^{n-1}$" should be -- 100 to 3000 $cPs^{n-1}$ --.

Signed and Sealed this

Third Day of July, 2001

Attest:

*Nicholas P. Godici*

NICHOLAS P. GODICI
*Attesting Officer*   *Acting Director of the United States Patent and Trademark Office*